US007775820B2

(12) United States Patent
McCauley et al.

(10) Patent No.: US 7,775,820 B2
(45) Date of Patent: Aug. 17, 2010

(54) HIGH TEMPERATURE CONNECTOR BODY (75) Inventors: Kathryn M. McCauley, Durand, MI (US); Charles Scott Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 12/143,321

(22) Filed: Jun. 20, 2008

(65) Prior Publication Data
US 2009/0318014 A1  Dec. 24, 2009

(51) Int. Cl.
*H01R 13/15* (2006.01)
(52) U.S. Cl. ..................................... 439/260
(58) Field of Classification Search ............... 439/260, 439/274, 275, 589, 913, 259, 261, 263, 265, 439/266, 711, 269.1, 262, 267; 174/84 C, 174/84 R; 204/424, 427
See application file for complete search history.

(56) References Cited

U.S. PATENT DOCUMENTS 6,615,641 B2 * 9/2003 Kojima ..................... 73/23.31
6,658,918 B2 * 12/2003 Hibino et al. .............. 73/31.05
6,878,252 B2    4/2005 Weyl et al.
2007/0072428 A1    3/2007 Chilcott

OTHER PUBLICATIONS

Co-pending U.S. Appl. No. 12/143,395, filed Jun. 20, 2008; Kathryn McCauley, Charles Scott Nelson; Connector Retainer.
Co-pending U.S. Appl. No. 12/143,523, filed Jun. 20, 2008; Kathryn McCauley, Charles Scott Nelson; High Temperature Connector.
Co-pending U.S. Appl. No. 12/143,505, filed Jun. 20, 2008; Kathryn McCauley, Charles Scott Nelson; Gas Sensor.
Co-pending U.S. Appl. No. 12/143,538, filed Jun. 20, 2008; Kathryn McCauley, Charles Scott Nelson; Radial Crimp Seal.

* cited by examiner

*Primary Examiner*—Javaid Nasri
(74) *Attorney, Agent, or Firm*—Thomas N. Twomey (57) ABSTRACT A ceramic connector body for a high temperature electrical connector, such as those used in high temperature gas sensors, incorporates a pair of opposing ceramic body portions which are operative for pivoting engagement and to be fixed in a connector body retainer which also enables their pivoting, hinged movement. The pivoting engagement permits the ceramic body portions to hinge open to receive a gas sensor with a low insertion force and a hinge close to provide the desired contact force. The ceramic body portions are also operative to house conductive terminals which provide electrical contact for power and signal communication with a gas sensor.

18 Claims, 7 Drawing Sheets

HIGH TEMPERATURE CONNECTOR BODY

TECHNICAL FIELD

An exemplary embodiment of the present invention relates generally to high temperature electrical connectors and, more particularly, ceramic connector bodies used therein.

BACKGROUND OF THE INVENTION

Combustion engines that run on fossil fuels generate exhaust gases. The exhaust gases typically include oxygen as well as various undesirable pollutants. Non-limiting examples of undesirable pollutants include nitrogen oxide gases (NOx), unburned hydrocarbon gases (HC), and carbon monoxide gas (CO). Various industries, including the automotive industry, use exhaust gas sensors to both qualitatively and quantitatively sense and analyze the composition of the exhaust gases for engine control, performance improvement, emission control and other purposes, such as to sense when an exhaust gas content switches from a rich to lean or lean to rich air/fuel ratio. For example, HC emissions can be reduced using sensors that can sense the composition of oxygen gas ($O_2$) in the exhaust gases for alteration and optimization of the air to fuel ratio for combustion.

A conventional high temperature gas sensor typically includes an ionically conductive solid electrolyte material, a porous electrode on the sensor's exterior exposed to the exhaust gases with a porous protective overcoat, a porous electrode on the sensor's interior surface exposed to a known gas partial pressure, an embedded resistance heater and electrical contact pads on the outer surface of the sensor to provide power and signal communication to and from the sensor. An example of a sensor used in automotive applications uses a yttria-stabilized, zirconia-based electrochemical galvanic cell with porous platinum electrodes to detect the relative amounts of oxygen present in an automobile engine's exhaust. When opposite surfaces of this galvanic cell are exposed to different oxygen partial pressures, an electromotive force (emf) is developed between the electrodes on the opposite surfaces of the electrolyte wall, according to the Nernst equation.

Exhaust sensors that include various flat-plate ceramic sensing element configurations formed of various layers of ceramic and electrolyte materials laminated and sintered together with electrical circuit and sensor traces placed between the layers, and embedded resistance heaters and electrical contact pads on the outer surface of the sensor to provide power and signal communication to and from the sensors have become increasingly popular. These flat-plate sensors generally have a sensing portion or end, that is exposed to the exhaust gases, and a reference portion or end, that is shielded from the exhaust gases providing an ambient reference. Gas sensors that employ these elements generally use high temperature electrical connectors for the electrical connection to contact pads on the reference end of the sensor to provide the necessary power and signal communication between a vehicle controller and the gas sensor. These electrical connectors are exposed to the extreme operating temperatures of internal combustion engine exhaust systems, which may include temperatures at the connector of greater than 200° C. and up to about 350° C. Thus, these connectors generally have connector bodies made from high temperature materials, such as ceramics.

These connectors also include conductive terminals which are generally disposed within the ceramic body portions and provide both contact portions to make the necessary electrical contact with the contact pads a termination portion for attachment to wires for communication with the controller. The connectors, including the ceramic body portions and terminals, must be designed so as to receive the ceramic gas sensor with a relatively low insertion force, but to have a relatively higher contact force in operation to ensure the reliability of the communications between the controller and the sensor. One such connector has proposed a clamshell configuration where opposing halves of a ceramic connector body open in a clamshell configuration to receive the gas sensor, whereupon the halves of the sensor are closed to establish electrical contact between conductive terminals disposed on the respective connector halves and the contact pads on the gas sensor. Upon closing the connector halves, a solid metal connector retaining ring is disposed around them to retain the connector body portions and establish the operating contact force between the terminals and the contact pads.

While various high temperature electrical connector configurations have been proposed, there remains a desire for improved high temperature connectors, including those having improved ceramic connector bodies and associated body portions.

SUMMARY OF THE INVENTION

In general terms, this invention provides an improved ceramic connector body for a high temperature electrical connector, such as those used in high temperature gas sensors, which incorporates a pair of opposing ceramic body portions which are operative for pivoting engagement and to be fixed in a connector body retainer which also enables their pivoting, hinged movement. The pivoting engagement permits the ceramic body portions to hinge open to receive a gas sensor with a low insertion force and a hinge close to provide the desired contact force. The ceramic body portions are also operative to house conductive terminals which provide electrical contact for power and signal communication with a gas sensor.

An exemplary embodiment of the present invention provides a ceramic connector body. The ceramic connector body includes a pair of ceramic body portions, each having a terminal side and a retainer side, a terminal end and a connection end, the terminal side having a pivot portion and a sensor pocket portion. The pivot portions and sensor pocket portions are adapted for disposition in opposing relation to form a sensor pocket and place the pivot portions in pivoting engagement.

The ceramic connector body may be configured to include a substantially circular or substantially rectangular cross-section. The ceramic connector body may further be configured to have a non-square, substantially rectangular cross-section.

The ceramic connector body portions may also be configured to include a pivot portion having a tapered section and a taper angle. The ceramic connector body portions may also be configured such that the taper angle is at least 5°.

The ceramic connector body portions may also be configured to include a retention pocket in the retainer side and an outwardly protruding retainer flange proximate one of the terminal end or the connection end. The retention pocket may be configured to taper inwardly away from the retainer flange.

The ceramic connector body portions may also be configured to include a plurality of terminal channels disposed between the terminal end and the connection end which extend into the sensor pocket. The ceramic connector body portions may also be configured such that each terminal channel has a terminal bore which extends from the terminal channel through the ceramic body portion and provides an opening in the retainer side. The ceramic connector body portions may also be configured such that outermost terminal channels define a first end wall and a second end wall, and an inner wall is located between the first end wall and a second end wall. The first end wall and a second end wall may be configured such that the first end wall has an extension which extends above the pivot portion and the second end wall has a cavity which is recessed from the pivot portion, and wherein the respective extensions and cavities of the respective ceramic body portions engage one another. The inner wall may be configured to include an inward protruding member which is offset from a centerline of the inner wall, and wherein the respective inward protruding members of the respective ceramic body portions provide a sensor stop.

The ceramic connector body portions may also be configured such that the ceramic body portions are identical.

The ceramic connector body portions may also be formed from a ceramic material comprising steatite.

Another exemplary embodiment of the present invention provides a ceramic connector body. The ceramic connector body includes a pair of ceramic body portions, each having a terminal side and a retainer side, a terminal end and a connection end, the terminal side having a pivot portion, a sensor pocket portion and a plurality of terminal channels disposed between the terminal end and the connection end which extend into the sensor pocket, the retainer side having a retention pocket. Each body portion also has an outwardly protruding retainer flange proximate one of the terminal end or the connection end. The pivot portions and sensor pocket portions are adapted for disposition in opposing relation to form a sensor pocket and place the pivot portions in pivoting engagement.

These and other features and advantages of this invention will become more apparent to those skilled in the art from the detailed description of a preferred embodiment. The drawings that accompany the detailed description are described below.

BRIEF DESCRIPTION OF THE DRAWINGS

The following is a brief description of the drawings wherein like elements are numbered alike in the several views.

DETAILED DESCRIPTION OF A PREFERRED EMBODIMENT

An exemplary embodiment of the present invention provides an improved ceramic connector body for a high temperature electrical connector suitable for use in a high temperature gas sensor. The ceramic connector body incorporates a pair of opposing ceramic body portions which are operative for pivoting engagement and to be fixed in a connector body retainer which also enables their pivoting, hinged movement. The pivoting engagement permits the ceramic body portions to hinge open to receive a gas sensor with a low insertion force and a hinge close to provide the desired contact force. The ceramic body portions may also include a taper section in a pivot portion with a taper angle that may be varied to control the pivoting, hinged movement of the electrical connector. The ceramic body portions may also include a retention pocket proximate to the connector body retainer for cooperation with outwardly extending arms of the retainer, as well as a protruding flange, for retention of the body portions in the retainer. The ceramic body portions may also include channels and associated bores for housing and retention of the conductive terminals, as well as features to assist in alignment of the of the gas sensor during insertion. A particular advantage of the ceramic connector body of the invention is that it may be used to provide a compact high temperature electrical connector, which in turn enables more compact gas sensors, including those having an M12×1.25 thread form, 14 mm wrench flats and an overall length of about 46.5 mm, a smaller lower shield having a diameter of only about 5.3 mm and protruding length of about 10.5 mm and a smaller sensor element having a width of about 2.4 mm, a length of about 27 mm and a thickness of about 0.82 mm. This small overall gas sensor profile provides much more flexibility in the mounting of the sensor, including access to various manifolds, conduits and other mounting points which were previously too small in themselves, or inaccessible due to the larger envelope of free space required to place or attach larger sensors due to the interference constraints associated with other vehicle or engine components. The reduced profile also provides a benefit with regard to material cost savings due to the reduced amounts of material required for most of the sensor components. The smaller thread size also enables mounting the sensors in smaller diameter and smaller length exhaust pipes and other conduits. Further, the smaller cross-section of the lower shield and sensing end of the sensor reduces intrusion into and interference with the exhaust stream. Still further, the smaller gas sensor houses a much smaller flat-plate ceramic sensing element that requires less power for activation (burn-off) of the sensor and a shorter sensor response times, thereby reducing the power load on the electrical systems and improving the responsiveness of the vehicle emission control systems of vehicles which utilize these sensors.

Figure 1:
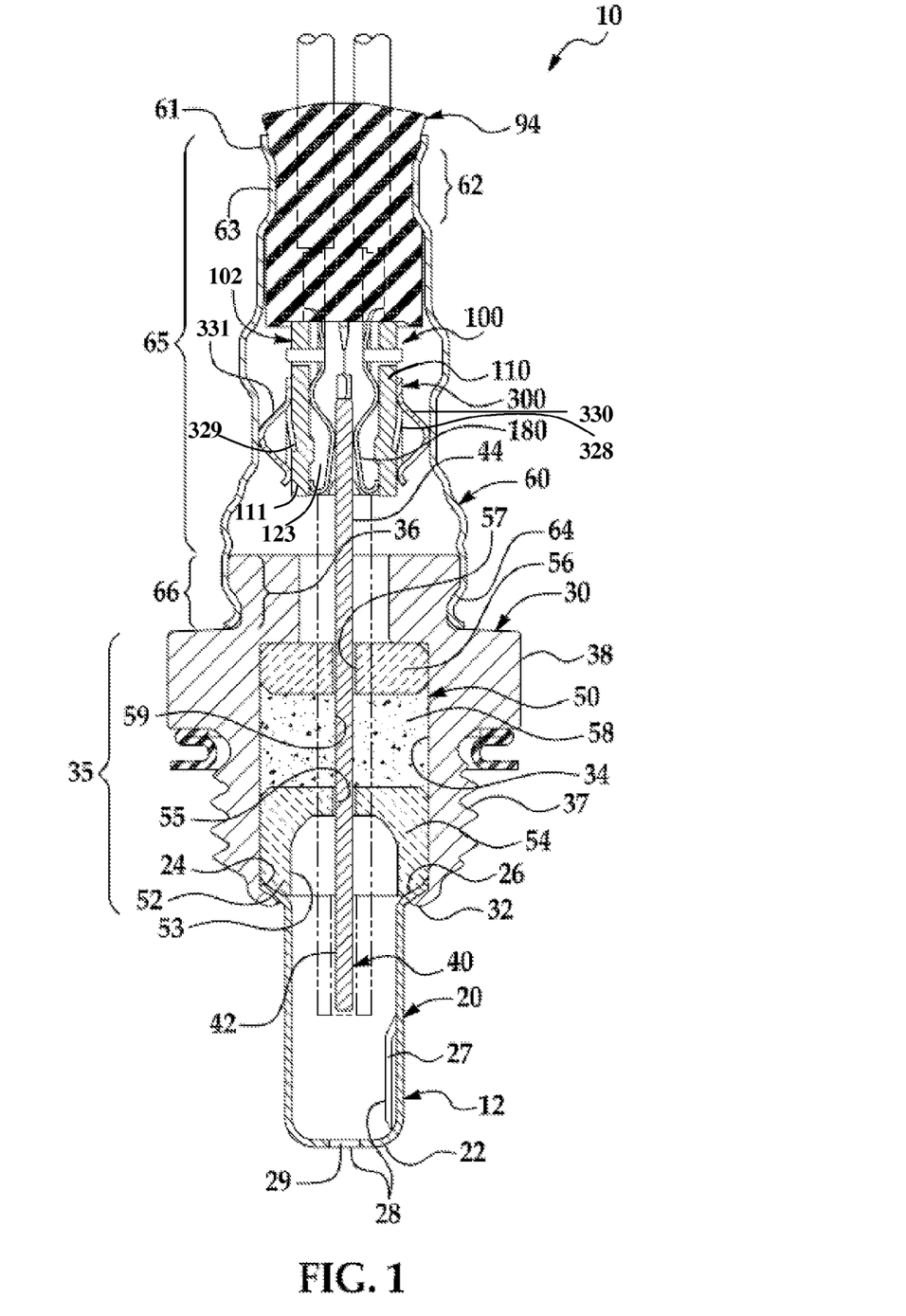
FIG. 1 is a cross-sectional view of an exemplary embodiment of a connector body retainer in a high temperature connector in a high temperature gas sensor according to the invention.

FIG. 1 illustrates a high-temperature gas sensor 10 which is adapted to qualitatively and quantitatively sense various exhaust gases, such as $O_2$, $NO_x$, HC, CO and the like, which incorporates an exemplary embodiment of the connector retainer body of the present invention. An exemplary embodiment of gas sensor 10 includes a generally cylindrical lower shield 20, sensor shell 30, flat-plate ceramic sensor 40, sensor packing 50, upper shield 60 and electrical connector assembly 100. Gas sensor 10 is suitable for exposure in a high temperature exhaust gas stream, including operating temperatures up to about 1000° C. at the sensing end 12 that is located in the exhaust gas stream, such as those found in the exhaust system of an internal combustion engine, including those used in many vehicular applications. Gas sensor 10 may be made in a compact form with an overall length of about 46.5 mm from the lower end of the lower shield to the upper end of the elastomeric seal.

Lower shield 20 is a substantially cylindrical form having a substantially closed end 22 and an open end 24. Open end 24 may include an outwardly extending flange 26 in the form of a straight taper or arcuate flair or other suitable flange form. Lower shield 20 is preferably formed of a metal which is adapted for high-temperature performance including resistance to high temperature oxidation and corrosion, particularly as found in high temperature exhaust gases and corrosive combustion exhaust byproducts associated with the exhaust stream of an internal combustion engine. Suitable metals include various ferrous alloys, such as stainless steels, including high chrome stainless steel, high nickel stainless steel, as well as various Fe-base, Ni-base, and Cr-base superalloys. The various ferrous and other alloys described above are generally indicative of a wide number of metal alloys that are suitable for use as lower shield 20. In an exemplary embodiment, lower shield 20 may be formed from type 310 stainless steel (UNS 31008) and may have an outer diameter of about 5.3 mm and an exposed length (i.e., below the deformed shoulder 32) of about 10.5 mm. Lower shield 20 abuts a lower end 62 of packing 50 and applies a compressive force thereto by the operation of deformed shoulder 32 at a lower end of shell 30. Deformed shoulder 32 presses against the outer surface of outwardly extending flange 26 and acts to retain both lower shield 20 and packing 50 within central bore 34 of shell 30. Lower shield 20 also includes one or more orifice 28 in the form of a bore 29, or louver 27 formed by piercing and inwardly bending the sidewall. Bore 29 may have any suitable shape, including various cylindrical, elliptical and slot-like shapes. Orifices 28 permit exhaust gases to enter the interior of lower shield 20 and come into contact with the lower or sensing end 42 of sensor 40 during operation of sensor 10, while at the same time, lower shield 20 provides a physical shield for sensor 40 against damage from the full fluid force of the exhaust gas stream, or from damage that may be caused by various mechanical or thermal stresses that result during installation or operation of sensor 10. While deformed shoulder 32 is illustrated for attachment of lower shield 20 in compressive engagement with packing 50, it will be appreciated that other means of attaching lower shield 20 to shell 30 while maintaining packing 50 in compressed engagement are possible, including various forms of weld joints, brazed joints and other attachment means and mechanisms.

In addition to deformed shoulder 32 and central bore 34, sensor shell 30 may be described generally as having an attachment portion 35 and a sealing portion 36. Attachment portion 35 may include a threaded form 37 which is adapted for threaded insertion and attachment into a component of the exhaust system of an internal combustion engine, such as an exhaust manifold or other exhaust system component, and tool attachment features 38, such as various forms of wrench flats (e.g. hex-shaped, double-hex and other wrench flat configurations). In an exemplary embodiment, shell 30 may have a thread form of M12×1.25 and a 14 mm hex wrench flats and be formed from Ni-plated steel. Shell 30 may be made from any material suitable for high-temperature exposure, including installation stresses associated with the threaded connection, mechanical stresses associated with usage of the device including various bending moments, thermal stresses and the like. Shell 30 will preferably be formed from a ferrous material, such as various grades of steel, including various plated or coated steels, such as those having various pure nickel or nickel alloy plating or coatings; however, the use of other metal alloys is also possible. While one embodiment of shell 30 is described herein, it will be appreciated by one of ordinary skill that many other forms of shell 30 may be used in conjunction with the present invention.

Referring again to FIG. 1, packing 50 is made up of a lower support disk 54, an upper support disk 56 and sealing member 58. Lower support disk 54 has a central slot 55 that is adapted to receive sensor 40 in closely spaced relation between slot 55 and the outer surface of sensor 40 proximate to slot 55. Generally, a substantially rectangular slot configuration provides closely spaced relation between lower support disk 54 and the outer surface of sensor 40. Lower support disk 54 may have a relieved portion 53 to provide spacing from sensor 40, and increase the exposure of the surface of sensor 40 to the exhaust gases that enter the interior of lower shield 20 during operation of sensor 10 in conjunction with operation of the associated internal combustion engine. Lower support disk 54 will generally be sized for slip-fit engagement with central bore 34 such that lower support disk 54 may be inserted into central bore 34 during assembly and yet have a minimal gap therebetween so as to reduce the tendency for leakage of exhaust gas between the outer surface of lower support disk 54 during operation of the sensor 10. The lower end 52 of the lower support disk 54 and central bore 34 may be tapered downwardly and inwardly or otherwise adapted for mating engagement with flange 26. Lower support disk 54 will generally be made from an electrically and thermally insulating, high-temperature ceramic material. Any suitable high-temperature ceramic material may be utilized, including various oxide, nitride or carbide ceramics or combinations thereof. Any suitable material may be utilized which is compatible with the function of sensor 40 and the operation of sealing member 58 in the high temperature operating environment of sensor 10.

The upper end of lower support disk 54 compressively engages sealing member 58. Sealing member 58 is preferably a compressed insulating powder, such as a talc disk. The compressed powder material of sealing member 58 is both electrically and thermally insulating. Sealing member 58 also has a central slot 59 that is adapted to receive sensor 40 in closely spaced relation between slot 59 and the outer surface of sensor 40 proximate to slot 59, particularly during installation of sealing member 58 over sensor 40. Upon installation of packing 50, including the compressive loading described herein, sealing member 58 is in compressed sealing engagement with the sensor 40 on the interior thereof, and shell 30 on the exterior thereof. Upon compressive installation of packing 50, sealing member 58 is operative to prevent passage of hot exhaust gases, particularly those received through orifices 28, from passing between the packing 50 and central bore 34 or along the surface of sensor 40 to an upper end 44 thereof.

Upper support disk 56 is in pressing engagement with sealing member 58 and is adapted to retain sealing member 58, such as by preventing it from being extruded through an upper portion of central bore 34. Upper support disk 56 also includes a central slot 57 that is adapted to receive sensor 40 in a similar manner as central slot 55 of lower support disk 54. Upper support disk 56 is likewise adapted for slip-fit engagement with central bore 34 in the manner described for lower support disk 54. Upper support disk 56 may be made from any suitable high temperature material, including ceramics or other materials identical to those used for lower support disk 54. However, upper support disk may also be made from a separate material, including a different ceramic material than that of lower support disk 54. Since upper support disk 56 is located further from the exhaust gas stream than lower support disk 54 and generally is exposed to somewhat lower temperatures than lower support disk 54, it may be desirable in some applications to make upper support disk 56 from a different material than that of lower support disk 54. While one configuration of packing 50 has been described, it will be appreciated that many other forms of packing 50 may be used in conjunction with the present invention.

High temperature gas sensor 40 may be of any suitable internal and external configuration and construction. Gas sensor 40, is preferably a flat-plate sensor having the shape of a rectangular plate or prism. Gas sensor 40 will typically include an ionically conductive solid electrolyte material, a porous electrode on the sensors exterior which is exposed to the exhaust gases, a porous protective overcoat, a porous electrode on the interior of the sensor which is adapted for exposure to a known gas partial pressure, an embedded resistance heater and various electrical contact pads on the outer surface of the sensor to provide the necessary circuit paths for power and signal communication to and from the sensor. Depending on the arrangement of the various elements described above, gas sensor may be configured to quantitatively, qualitatively, or both, sense various constituents of the exhaust gas, including $O_2$, $NO_x$, HC and CO. For automotive applications, an example of a suitable construction of sensor 40 would include a yttria-stabilized, zirconia-based electrochemical galvanic cell with porous platinum electrodes to detect the relative amounts of oxygen present in engine exhaust. When opposite surfaces of such a galvanic cell located at sensing end 42 and reference end 44 are exposed to different oxygen partial pressures, an electromotive force (emf) is developed between electrodes located at these ends on the opposite surfaces of the electrolyte wall according to the Nernst Equation. In an exemplary embodiment, gas sensor may have the shape of a rectangular prism having a width of about 2.4 mm, a length of about 27 mm and a width of about 0.82 mm. While an exemplary embodiment of gas sensor 40 is described above, various configurations of gas sensor 40 are contemplated for use in conjunction with the exemplary embodiment of the invention, including gas sensors 40 which are adapted for sensing other exhaust gas constituents, and further including gas sensors having other dimensions and flat-plate configurations.

Figure 2:
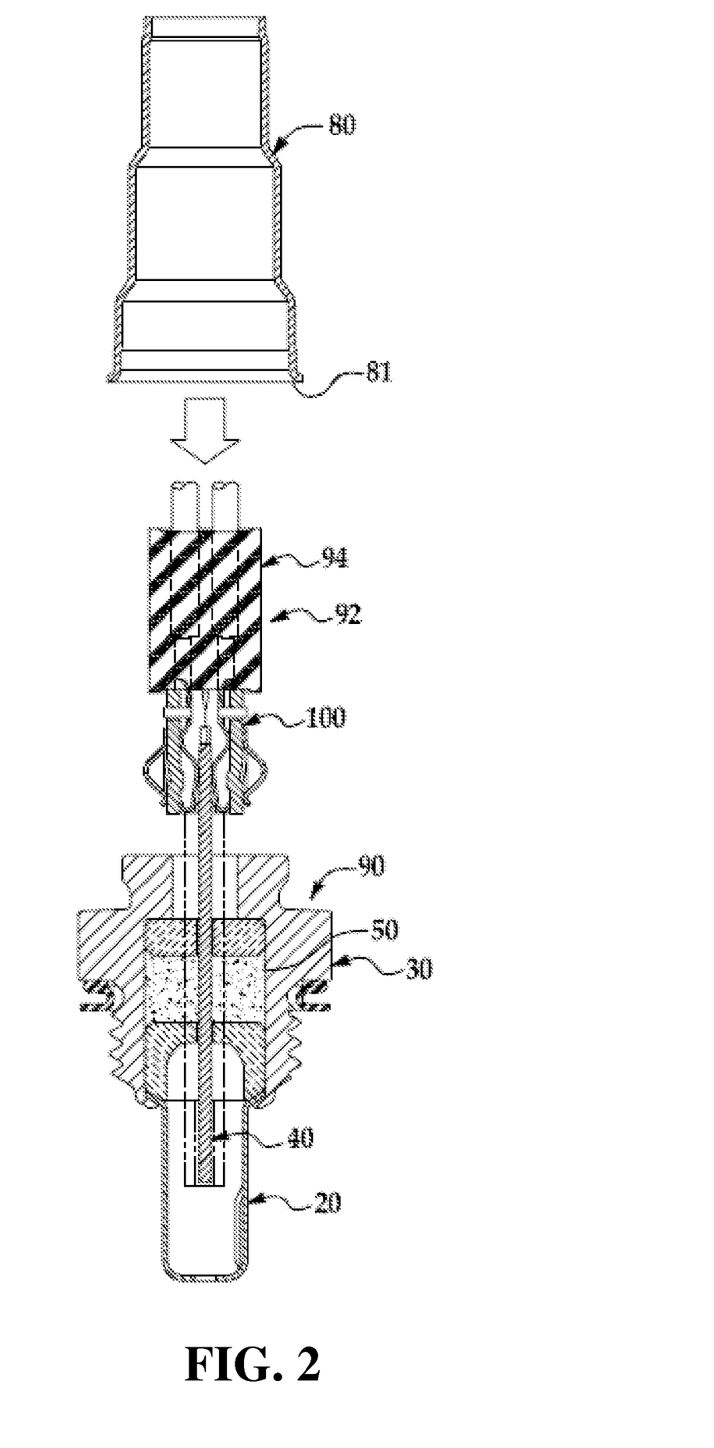
FIG. 2 is a schematic cross-sectional view illustrating the insertion of a precursor upper shield onto a sensor-connector subassembly.
Figure 3:
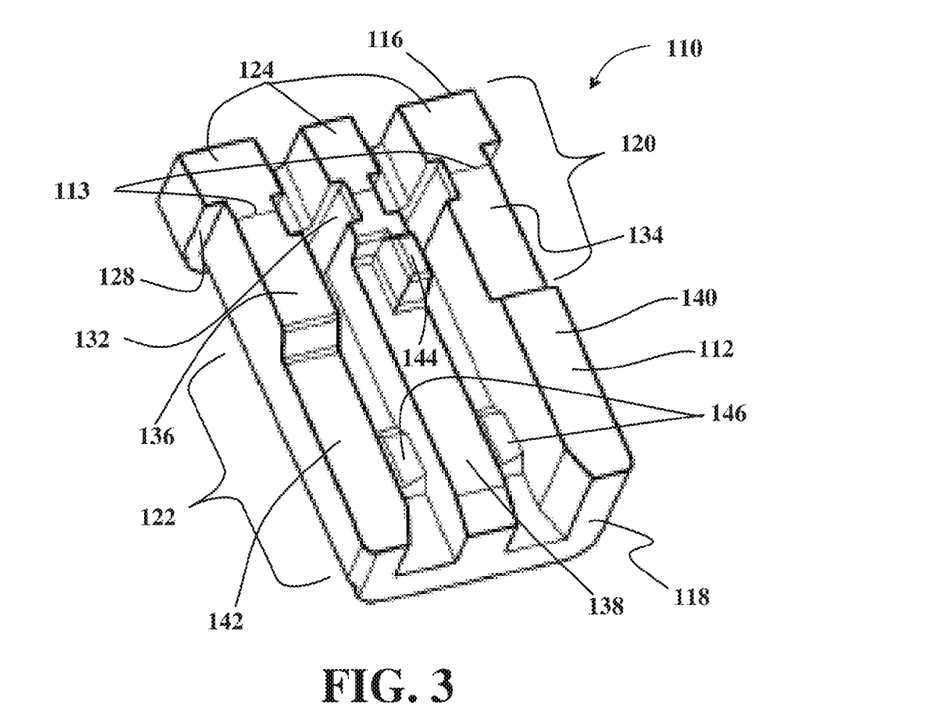
FIG. 3 is an front perspective view of an exemplary embodiment of a connector body portion of the present invention.

Referring to FIG. 2, in an exemplary embodiment, the lower shield 20, sensor shell 30, gas sensor 40 and packing 50 may be assembled in the manner described herein to form a sensor subassembly 90. The electrical connector 100 is inserted onto the sensor subassembly 90 by insertion of the upper or reference end 44 of sensor 40 into a sensor pocket on the insertion end of electrical connector 100, as shown in FIG. 2, to form a sensor/connector subassembly 92. Electrical connector 100 hinges open to receive sensor 40. It is preferred that sensor 40 and electrical connector 100 be configured so that upon insertion of the sensor subassembly 90, sufficient power and signal communication are established between the conductive terminals 180 of the electrical connector 100 and the electrical contacts (not shown) of sensor 40 to pretest the electrical connections between them. Once the necessary electrical connections are assured, the assembly of gas sensor 10 is completed by the addition of upper shield of 60 which is formed from the precursor upper shield 80, as shown in FIG. 2.

Figure 6:
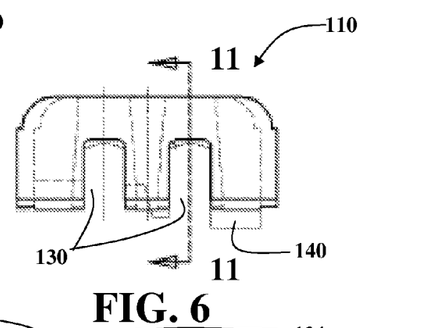
FIG. 6 is a top view of the connector body portion of FIG. 3.
Figure 7:
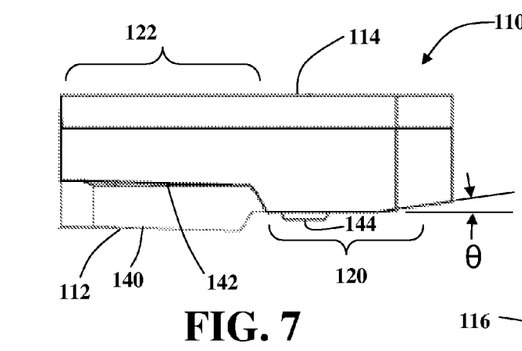
FIG. 7 is a left side elevational view of the connector body of FIG. 3.

Referring again to FIG. 2, the precursor upper shield 80 is installed over the sensor-connector subassembly 92 (FIG. 6) to the position shown in FIG. 7 so that the upper end 81 of precursor upper shield is located proximate, preferably in touching contact with, an upper shoulder of tool attachment feature 38. Precursor upper shield 80 is preferably formed of a metal that is adapted for high-temperature performance including resistance to high temperature oxidation and corrosion, particularly as found in high temperature exhaust gases and corrosive combustion exhaust byproducts associated with the exhaust stream of an internal combustion engine. Suitable metals include various ferrous alloys, such as stainless steels, including high chrome stainless steel, high nickel stainless steel, as well as various Fe-base, Ni-base, and Cr-base superalloys. The various ferrous and other alloys described above are generally indicative of a wide number of metal alloys that are suitable for use as precursor upper shield 80. In an exemplary embodiment, precursor upper shield 80 may be formed from type 304 stainless steel (UNS 30400). In an exemplary embodiment, precursor upper shield 80 may have an overall length of about 22 mm and an inner diameter that varies in three cylindrical sections of decreasing diameter from top to bottom of about 7 mm to about 11 mm. The precursor upper shield 80 is deformed, such as by crimping, to form upper shield 60.

Upper shield 60 is formed from a precursor upper shield 80, such as that shown in FIG. 2. A gas-tight upper sealed joint 62 is formed in sensor 10 when precursor upper shield 80 as shown in FIG. 2 is plastically deformed into upper shield 60 having the shape shown in FIG. 1. This deformation may include a plurality of crimps formed along the length of precursor upper shield 80. A gas-tight upper sealed joint 62 is formed when precursor upper shield 80 as shown in FIG. 2 is crimped and plastically deformed into upper shield 60 having the shape shown in FIG. 1. Crimp 63 provides pressing engagement between an inner surface of the upper end of upper shield 60 and an outer surface of elastomeric sealing member 94. Crimp 63 deforms precursor upper shield 80 at an upper end 82 thereof sufficiently to provide pressing engagement between upper shield 60 and elastomeric sealing member 94, including the deformation of elastomeric sealing member 94, thereby forming upper sealed joint 62. While shown as a single radial crimp 63 in FIG. 1, upper sealed joint 62 may also be formed by a plurality of radial crimps of the type described herein. Upper shield 60 has a shell portion 66 and a connector portion 65 that extends upwardly and away from shell 30 and generally includes the portions of upper shield 60 other than shell portion 66.

Sensor 10 also includes a lower sealed joint 64 between sealing portion 36 of shell 30 and the shell portion 66 of upper shield 60. Referring now to FIG. 1, lower sealed joint 64 is a gas-tight sealed joint formed between the outer surface of sealing portion 36 of shell 30 and the inner surface of the shell portion 66 of upper shield 60. Lower sealed joint 64 is formed when precursor upper shield 80 is crimped and plastically deformed into upper shield 60 having the shape shown in FIG. 1.

Referring again to FIG. 1, electrical connector 100 is adapted to provide an electrical connection for power and signal communication between sensor 40 and a device that is adapted to receive such communications, such as an engine or other controller while at the same time providing the required electrical isolation between the various circuit paths associated with the required power and signal communication. Electrical connector 100 is in spring-biased engagement within an upper end 61 of upper shield 60 through outwardly extending spring arms 320 associated with the connector body retainer 300. Electrical connector 100 is a clamshell configuration of a pair of ceramic connector body portions 110,111 that are housed and retained in connector body retainer 300. The spring-bias closes the clamshell and ensures a sufficient contact pressure between the conductive terminals 180 of the connector and electrical contacts (not shown) located on the upper end 44 of sensor 40 to provide a low resistance electrical connection sufficient for signal and power communication between sensor 40 and a device, such as a controller, which is adapted to receive the signal.

Figure 9:
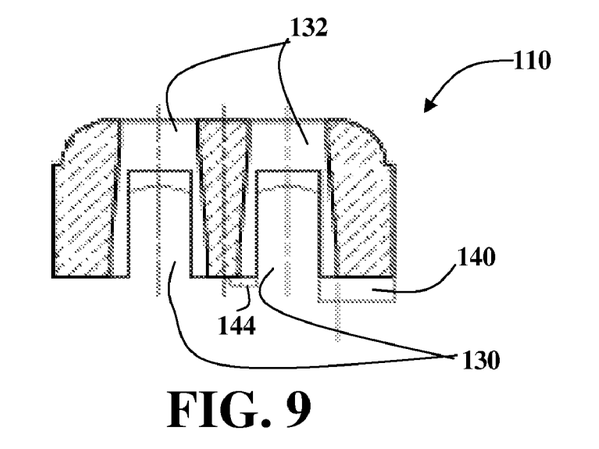
FIG. 9 is a cross-section of the connector body portion of FIG. 3 taken along Section 9-9.
Figure 10:
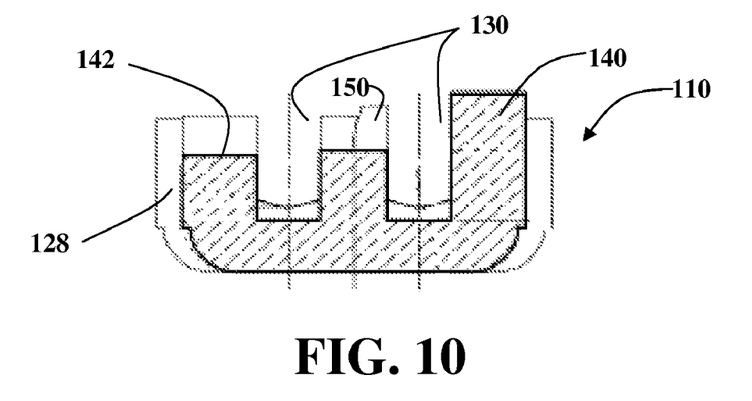
FIG. 10 is a cross-section of the connector body portion of FIG. 3 taken along Section 10-10.

Referring to FIGS. 1-2, an exemplary embodiment of the present invention provides a connector body 102. Ceramic connector body 102 provides a suitable structure for housing conductive terminals 180. It provides a physical structure for attachment and positioning of conductive terminals 180, as well as providing electrical isolation between them. Ceramic connector body 102 cooperates with conductive terminals 180, as well as connector body retainer 300 to provide electrical contact to gas sensor 40 for power and signal communication between the sensor and a controller (not shown). Ceramic connector body 102 may have, and ceramic body portions 110,111 may be configured to provide, a substantially rectangular outer profile or cross-section, as may be understood from the partial profile that is shown, for example, in FIGS. 6 and 9, where, but for the rounded corners, the full body profile is substantially rectangular. In this embodiment, ceramic connector body 102 has the shape of a substantially rectangular prism. It is believed that ceramic connector body 102 may have, and ceramic body portions 110,111 may also be configured to provide, other shapes, including a substantially circular outer profile or cross-section (not shown). This would provide a ceramic connector body 102 with the shape of a cylinder. The ceramic connector body 102 may further be configured to have a non-square, substantially rectangular outer profile or cross-section. This configuration is advantageous in that it greatly reduces or eliminates the possibility of mis-orientation of the ceramic connector body 102 within the connector body retainer 300 during their assembly.

Referring to FIGS. 1-11, 16 and 17, the ceramic connector body 102 includes a pair of ceramic body portions 110,111 (as shown in FIGS. 1 and 2). Body portions 110 may have an identical configuration; however, the various features of body portions 110 described herein may also be incorporated in non-identical body portion configurations. Since the body portions are identical in the exemplary embodiments described herein, except for FIGS. 1 and 2, reference is made only with respect to body portion 110. Ceramic body portions 110 may be made from any suitable ceramic material. In an exemplary embodiment, ceramic body portions 110 may be made from steatite. Ceramic body portions 110 may be made using any suitable method for forming them, including the various body features described herein, such as various molding and sintering methods.

Each body portion 110 has a terminal side 112 and a retainer side 114. Terminal side 112 is the side on which the terminals are housed. Retainer side 114 is the side which faces connector body retainer 300. Each body portion 110 also has a terminal end 116 and a connection end 118. Terminal and 116 is the end through which terminals extend for interconnection with wires (FIGS. 1 and 2) used to provide signal and power communication with a controller. Connection end 118 is the end that faces the gas sensor 40.

Terminal side 112 has a pivot portion 120 and a sensor pocket portion 122. The pivot portions 120 and sensor pocket portions 122 of a given pair of body portions 110 are adapted for disposition in opposing relation. In this opposing relation, the sensor pocket portions 122 provide a sensor pocket 123 between them and the pivot portions 120 are in touching contact, as illustrated in FIGS. 1 and 2. The sensor pocket 123, and sensor pocket portions 122, is designed with regard to size and shape so as to be operative to receive the reference end of gas sensor 40. The pivot portions 120 are configured such that they are operative for pivoting engagement (as shown in FIGS. 1 and 2) to enable the electrical connector to hinge open and hinge closed in the manner described herein. Pivot portion 120 may comprise a flat planar structure, and may include a plurality of intersecting flat planes as shown, for example, in FIG. 3, where opposing body portions 110 pivot generally about the line 113 formed by the intersection of the planes. However, it is believed that alternate structures of the pivot portion 120, for example, such as one having an arcuate region where the flat planes intersect, or one having an inwardly convex (convex in the direction of the mid-plane) curvature, would also work in accordance with the invention described herein. The pivot portion 120 may include a tapered section 124 and a taper angle (θ), as shown, for example, in FIGS. 3, 5 and 7. Ceramic connector body portions 110 may also be configured such that the taper angle is at least 5°. The taper angle (θ) may be selected to provide the desired degree of hinged opening of the ceramic connector body 102 within connector body retainer 300 for insertion of gas sensor 40.

Figure 4:
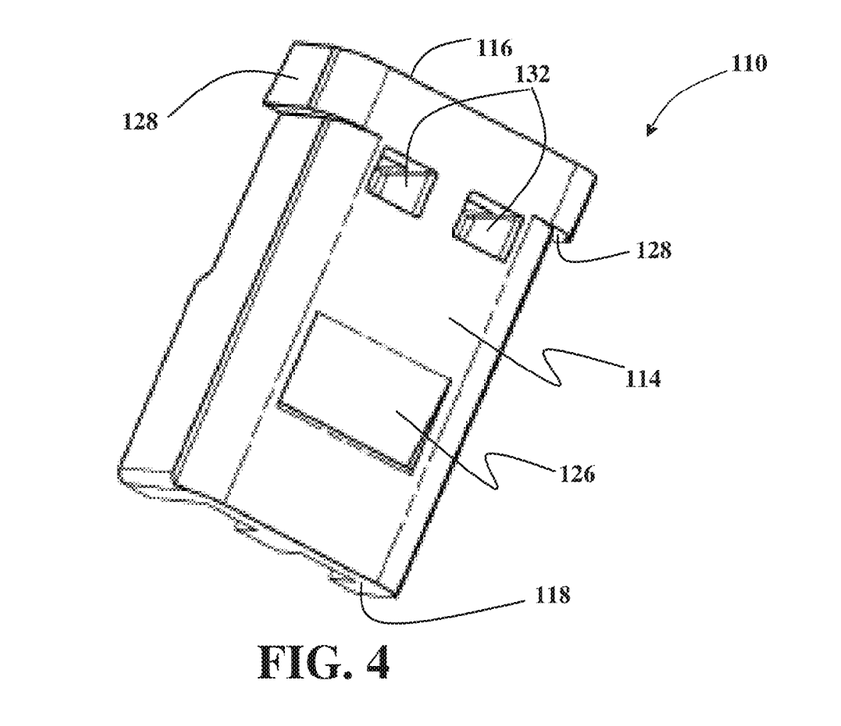
FIG. 4 is an rear perspective view of the connector body portion of FIG. 3.
Figure 5:
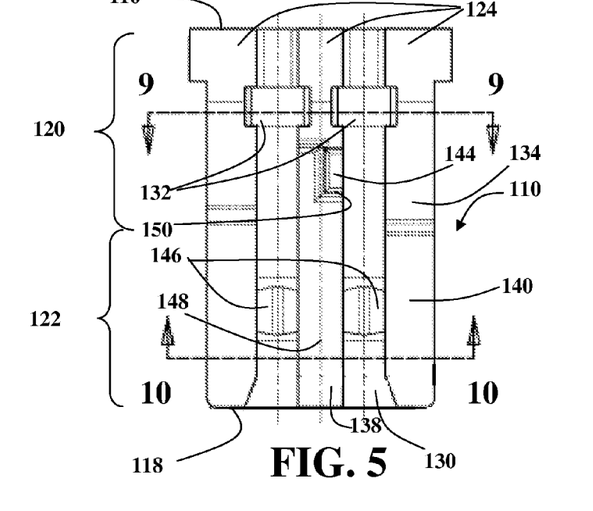
FIG. 5 a front view of the connector body portion of FIG. 3.
Figure 8:
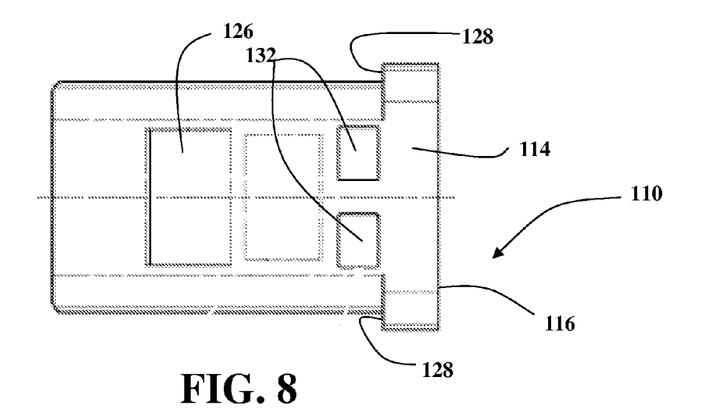
FIG. 8 is a rear view of the connector body portion of FIG. 3
Figure 11:
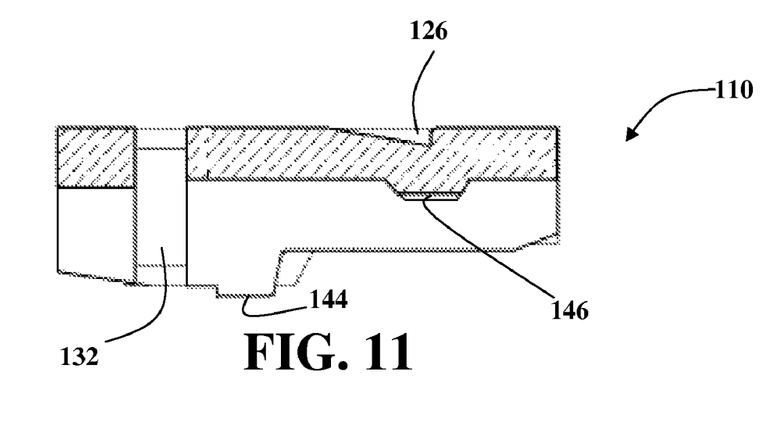
FIG. 11 is a cross-section of the connector body portion of FIG. 6 taken along Section 11-11.
Figure 12:
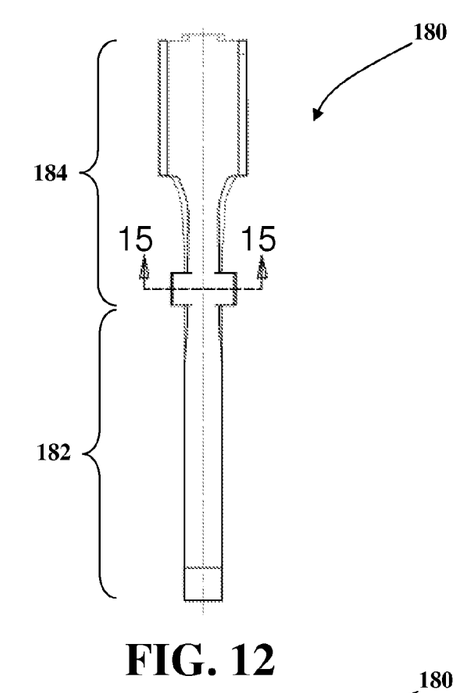
FIG. 12 is a front view of an conductive terminal in accordance with another exemplary embodiment of the invention.
Figure 13:
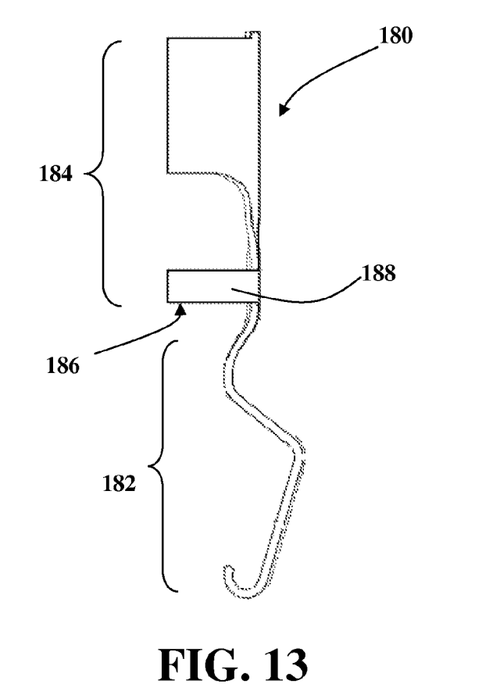
FIG. 13 is a side view of the conductive terminal of FIG. 12
Figure 14:
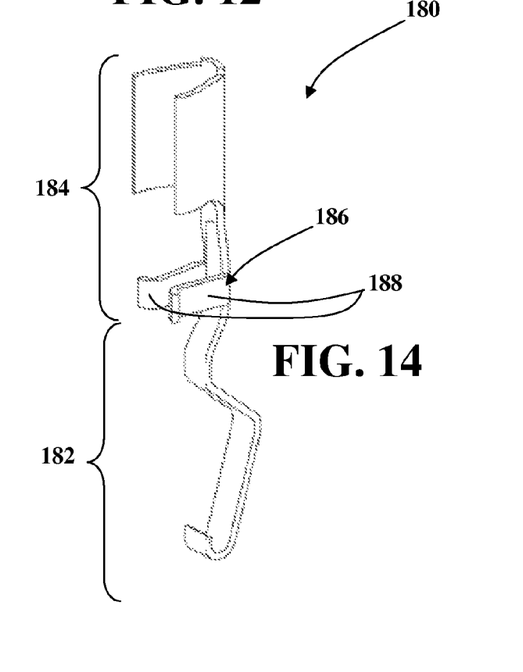
FIG. 14 is a front perspective view of the conductive terminal of FIG. 12.
Figure 15:
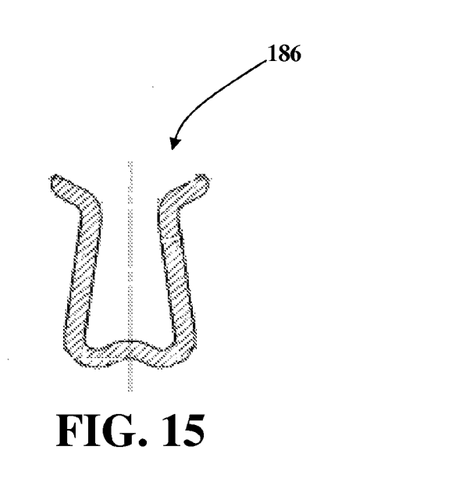
FIG. 15 is a cross-sectional view of the conductive terminal of FIG. 12 taken along Section 15-15.

Referring to FIGS. 4, 8 and 11, ceramic connector body portions 110 may also be configured to include a retention pocket 126 in the retainer side 114 and an outwardly protruding retainer flange 128 proximate one of the terminal end 116 or the connection end 118. Retention pocket 126 may have any suitable shape and configuration. Retention pocket 126 may be shaped so as to permit the capture of inwardly extending arms 328,329 of connector body retainer 300 upon insertion of ceramic connector body 102 and body portions 110 therein, as shown in FIGS. 1 and 2. Retention pockets 126 may be configured to taper inwardly away from the retainer flange 128, as shown in FIGS. 4 and 8. As also shown in FIGS. 4 and 8, retainer flanges 128 are located proximate terminal ends 116. Retainer flanges 128 are configured to abut hinge ends 322,323 of connector body retainer 300. The retention pockets 126 and retainer flanges cooperate with the respective features of connector body retainer 300 described above to capture ceramic connector body portions 110 in retainer 300. It is believed that retainer flanges 128 may be located proximate either the terminal end 116 or the connection end 118, with respective suitable rearrangement of the orientation of retention pockets 126 and retainer 300.

Ceramic connector body portions 110 may also be configured to include a plurality of terminal channels 130 disposed between the terminal end 116 and the connection end 118 which extend into the sensor pocket 124. The plurality of terminal channels 130 are adapted house and retain a corresponding plurality of electrical terminals 180 within the terminal channels 130 in electrical isolation from all non-associated conductive terminals. In the exemplary embodiments of FIGS. 3-17, only two channels are shown; however, any number of additional channels may be incorporated to house additional terminals, such 3, 4, 5, 6 or more terminal configurations.

Figure 16:
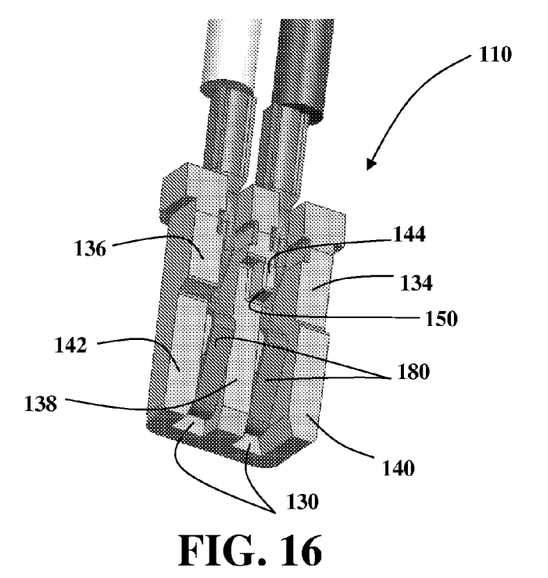
FIG. 16 is a front perspective view of a connector body and conductive terminal assembly in accordance with another exemplary embodiment of the invention.
Figure 17:
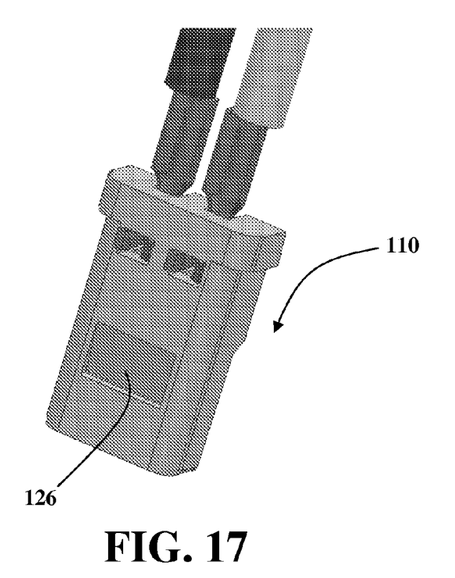
FIG. 17 is a rear perspective view of the connector body and conductive terminal assembly of FIG. 16.

Referring to FIGS. 12-17, electrical or conductive terminals 180 have a contact portion 182 and a termination portion 184. Any suitable configuration of conductive terminal 180 may be used. In an exemplary embodiment, contact portion 182 has an inwardly-bent bow configuration. The inwardly-bent bow configuration of contact portion 182 acts as a spring member upon hinged closure of the electrical connector upon the gas sensor in the manner shown in FIGS. 1 and 2 to establish a spring bias electrical contact with contact pads of the gas sensor and provide a sufficient contact force to establish and ensure reliable signal and power communication between the sensor and a controller. The termination portion 184 also includes an attachment tang 186. In an exemplary embodiment, attachment tang 186 is substantially u-shaped with a pair of inwardly arched legs 188. The inwardly arched legs 188 may be compressed as a spring member in conjunction with insertion in a terminal bore 132, such that upon full insertion, the legs 188 flex outwardly over an outer edge of the bore, thereby capturing tang 186 in terminal bore 132 and conductive terminal 180 within terminal channel 130, as shown in FIGS. 16 and 17. Conductive terminals 180 may be made from any suitable conductive material. In an exemplary embodiment, conductive terminals 180 are made from stainless steel, with a coating of a conductive material, such as gold, having better electrical conductivity than stainless steel and high temperature oxidation and corrosion resistance.

Referring, for example, to FIGS. 1, 2, 5 and 8, ceramic connector body portions 110 may also be configured such that each terminal channel 130 has a terminal bore 132 which extends from terminal channel 130 through ceramic body portion 110 and provides an opening in retainer side 114.

Ceramic connector body portions 110 may also be configured such that outermost terminal channels (in FIGS. 3-17 there are only two, so both are outermost) define a first end wall 134 and a second end wall 136, and an inner wall 138 is located between first end wall 134 and second end wall 136. In an exemplary embodiment, the first end wall 134 and second end wall 136 may be configured such that first end wall 134 has an extension or extended portion 140 which extends above pivot portion 124 and second end wall 136 has a cavity 142 which is recessed from pivot portion 124, and wherein the respective extensions 140 and cavities 142 of the respective ceramic body portions 110 engage one another in mating or nested engagement. Extensions 140 extend above a mid-plane of the ceramic body 102 and sensor pocket 123 (i.e., a central cutting plane along the length of gas sensor 40 of FIG. 1 that passes between the opposed pivot portions) and cavities 142 are recessed below it. In this configuration, extensions 140 and cavities 142 prevent the mis-alignment of gas sensor within the sensor pocket 123 because the respective extensions 140 on either side act as lateral or side stops preventing the sensor from inadvertently slipping out of the pocket during its insertion. The inner wall 138 may be configured to include an inwardly protruding member 144 which is offset from a centerline 148 of the inner wall, and wherein the respective inward protruding members 144 of the respective ceramic body portions 110 together provide a sensor stop surface 150 at the lower end of sensor pocket 123. Ceramic connector body portions 110 may also be configured such that terminal channels also include a protrusion 146 opposite the retention pocket 126 which provides addition thickness of the body portion wall located thereunder, thereby strengthening the sidewall of ceramic body portions at that location.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A ceramic connector body, comprising: a pair of ceramic body portions, each having a terminal side and a retainer side, a terminal end and a connection end, the terminal side having a pivot portion and a sensor pocket portion, the pivot portions and sensor pocket portions adapted for disposition in opposing relation to form a sensor pocket and place the pivot portions in pivoting engagement, and wherein outermost terminal channels define a first end wall and a second end wall, and an inner wall is located between the first end wall and the second end wall, and wherein the inner wall has an inward protruding member which is offset from a centerline of the inner wall, and wherein the respective inward protruding members of the respective ceramic body portions provide a sensor stop.

2. The ceramic connector body of claim 1, wherein the ceramic connector body has a substantially circular or substantially rectangular cross-section.

3. The ceramic connector body of claim 1, wherein the ceramic connector body has a non-square, substantially rectangular cross-section.

4. The ceramic connector body of claim 1, wherein each pivot portion has a tapered section having a taper angle.

5. The ceramic connector body of claim 4, wherein the taper angle is at least 5°.

6. The ceramic connector body of claim 1, wherein each of the ceramic body portions further comprises a retention pocket in the retainer side and an outwardly protruding retainer flange proximate one of the terminal end or the connection end.

7. The ceramic connector body of claim 6, wherein each retention pocket tapers inwardly away from the retainer flange.

8. The ceramic connector body of claim 1, wherein each of the terminal sides has a plurality of terminal channels disposed between the terminal end and the connection end which extend into the sensor pocket.

9. The ceramic connector body of claim 8, wherein each terminal channel has a terminal bore which extends from the terminal channel through the ceramic body portion and provides an opening in the retainer side.

10. The ceramic connector body of claim 1, wherein the first end wall has an extension which extends above the pivot portion and the second end wall has a cavity which is recessed from the pivot portion, and wherein the respective extensions and cavities of the respective ceramic body portions engage one another when two of the ceramic connector body portions are disposed in an orientation such that the respective terminal sides are mated together.

11. The ceramic connector body of claim 1, wherein the ceramic body portions are identical.

12. The ceramic connector body of claim 1, wherein each of the ceramic body portions is formed from a ceramic material comprising steatite.

13. A ceramic connector body, comprising:
a pair of ceramic body portions, each having a terminal side and a retainer side, a terminal end and a connection end, the terminal side having a pivot portion, a sensor pocket portion and a plurality of terminal channels disposed between the terminal end and the connection end which extend into the sensor pocket portion wherein outermost terminal channels define a first end wall and a second end wall, and an inner wall is located between the first end wall and the second end wall, the retainer side having a retention pocket, each body portion also having an outwardly protruding retainer flange proximate one of the terminal end or the connection end, wherein each retention pocket tapers inwardly away from the retainer flange, the pivot portions and sensor pocket portions adapted for disposition in opposing relation to form a sensor pocket and place the pivot portions in pivoting engagement, and wherein the inner wall has an inward protruding member which is offset from a centerline of the inner wall, and wherein the respective inward protruding members of the respective ceramic body portions provide a sensor stop.

14. The ceramic connector body of claim 13, wherein each pivot portion has a tapered section having a taper angle.

15. The ceramic connector body of claim 14, wherein the taper angle is at least 5°.

16. The ceramic connector body of claim 13, wherein each terminal channel has a terminal bore which extends from the terminal channel through the ceramic body portion and provides an opening in the retainer side.

17. The ceramic connector body of claim 13, wherein the first end wall has an extension which extends above the pivot portion and the second end wall has a cavity which is recessed from the pivot portion, and wherein the respective extensions and cavities of the respective ceramic body portions are operative to engage one another when two of the ceramic connector body portions are disposed in an orientation such that the respective terminal sides are mated together.

18. The ceramic connector body of claim 13, wherein each of the ceramic body portions is formed from a ceramic material comprising steatite.

\* \* \* \* \*